US 6,685,950 B2

(12) United States Patent
Weber et al.

(10) Patent No.: US 6,685,950 B2
(45) Date of Patent: Feb. 3, 2004

(54) METHODS OF TREATING VIRAL INFECTIONS

(75) Inventors: Olaf Weber, Woodbridge, CT (US); Tobias Schlapp, Köln (DE); Angela Siegling, Paris (FR); Andreas Knorr, Erkrath (DE); Claudia Hirth-Dietrich, Wuppertal (DE); Gudrun Theiss, Wuppertal (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/903,013

(22) Filed: Jul. 11, 2001

(65) Prior Publication Data

US 2003/0021769 A1 Jan. 30, 2003

(30) Foreign Application Priority Data

Jul. 11, 2000 (DE) ........................................... 10033582
May 9, 2001 (DE) ........................................... 10122451

(51) Int. Cl.$^7$ ............................................... A61K 45/00
(52) U.S. Cl. ............................... 424/281.1; 424/232.1; 435/235.1
(58) Field of Search ........................... 514/2; 424/199.1, 424/202.1, 204.1, 225.1, 226.1, 227.1, 232.1, 281.1; 435/235.1

(56) References Cited

U.S. PATENT DOCUMENTS 4,191,745 A * 3/1980 Mayr et al. ................... 424/90
5,443,964 A * 8/1995 Pickup et al. ............... 435/69.1
6,365,393 B1 * 4/2002 Schmeer et al. .......... 435/235.1

FOREIGN PATENT DOCUMENTS

WO       9522978        8/1995
WO       97/37031    * 10/1997

OTHER PUBLICATIONS

Gel filtration theory and practice handbook published by Pharmacia Fine Chemicals, Sweden, 1979, pp. Introduction, Principle, and 24.*

Lucin, P., Jonjic, S., Messerle, M., Polic, B., Hengel, H., Koszinowski, U., "Late Phase Inhibition of Murine Cytomegalovirus Replication by Synergistic Action of Interferon-gamma and Tumour Necrosis Factor", J. of Gen. Virology 75: 101–110 (1994).

Smith, P., Wolcott, R., Chervenak, R., Jennings, S., Control of Acute Cutaneous Herpes Simplex Virus Infection: T Cell–Mediated Viral Clearance Is Dependent upon Interferon–γ (IFN–γ), Virology 202: 76–88 (1994).

Kawanishi, Y., Hayashi, N., Katayama, K., Ueda, K., Takehara, T., Miyoshi, E., Mita, E., Kasahara, A., Fusamoto, H., Kamada, T., "Tumor Necrosis Factor–α and Interferon–γ Inhibit Synergistically Viral Replication in Hepatitis B Virus–Replicating Cells", J. of Med. Virology 47: 272–277 (1995).

Dhawan, S., Wahl, L., Heredia, A., Zhang, Y., Epstein, J., Melzer, M., Hewlett, I., "Interferon–γ Inhibits HIV–induced Invasiveness of Monocytes", J. or Leukocyte Biology 58: 713–716 (1995).

Bromberg, J., Horvath, C., Wen, Z., Schreiber, R., Darness, J., "Transcriptionally Active Stat1 is Required for the Antiproliferative Effects of Both Interferon α and Interferon γ", Proc. Natl. Acad. Sci. USA 93: 7673–7678 (1996).

Klouche, M., Kirchner, H., Holzel F., "Antiproliferative Effects of Interferon γ in Combination with α–difluoromethylornithine on Human Carcinoma Cell Cultures", J. Cancer Res. Clin. Oncol. 120: 700–706 (1994).

Guidotti, L., Borrow, P., Hobbs, M., Matzke, B., Gresser, I., Oldstone, M., Chisari, F., "Viral Cross Talk: Intracellular Inactivation of the Hepatitis B Virus During an Unrelated Viral Infection of the Liver", Proc. Natl. Acad. Sci. USA 93: 4589–4594 (1996).

Guidotti, L., Ando, K., Hobbs, M., Ishikawa, T., Runkel, L., Schreiber, R., Chisari, F., "Cytotoxic T Lymphocytes Inhibit Hepatitis B Virus Gene Expression by a Noncytolytic Mechanism in Tansgenic Mice", Proc. Natl. Acad. Sci. USA 91: 3764–3768 (1994).

Steinmassl, M., Wolf, G., "Bildung Von Interleukin–2 und Interferonα Durch Mononukleare Leukozyten des Schweines Nach In Vitro–stimulation Mit Verschiedenen Viruspraparaten", J. Vet. Med. 37: 321–331 (1990) Considered Only to the Extent of the English Abstract.

* cited by examiner

Primary Examiner—Jeffrey Stucker
(74) Attorney, Agent, or Firm—Susan M. Pellegrino (57) ABSTRACT

The present invention relates to the use of strains of Parapoxvirus ovis as immunotherapeutic agents for immunodeficiencies of an infectious or non-infectious nature, and to the use of strains of Parapoxvirus ovis for treating tumor diseases and viral infections, and diseases which accompany them, and the use of strains of Parapoxvirus ovis for producing medicaments for use in humans and animals.

11 Claims, 10 Drawing Sheets

SEQUENCE LISTING

```
<160> NUMBER OF SEQ ID NOS: 11

<210> SEQ ID NO 1
<211> LENGTH: 25
<212> TYPE: DNA
<213> ORGANISM: Mus sp.

<400> SEQUENCE: 1
taaaacgcag ctcagtaaca gtccg                                           25

<210> SEQ ID NO 2
<211> LENGTH: 25
<212> TYPE: DNA
<213> ORGANISM: Mus sp.

<400> SEQUENCE: 2
tggaatcctg tggcatccat gaaac                                           25
```

```
<210> SEQ ID NO 3
<211> LENGTH: 26
<212> TYPE: DNA
<213> ORGANISM: Hepatitis B virus

<400> SEQUENCE: 3
ccatcatcct gggctttcgg aaaatt                                              26

<210> SEQ ID NO 4
<211> LENGTH: 19
<212> TYPE: DNA
<213> ORGANISM: Hepatitis B virus

<400> SEQUENCE: 4
aggagaaacg ggctgaggc                                                      19

<210> SEQ ID NO 5
<211> LENGTH: 21
<212> TYPE: DNA
<213> ORGANISM: Hepatitis B virus

<400> SEQUENCE: 5
ctgtaccaaa ccttcggacg g                                                   21

<210> SEQ ID NO 6
<211> LENGTH: 24
<212> TYPE: DNA
<213> ORGANISM: Mus sp.

<400> SEQUENCE: 6
gtcacagttt tcagctgtat aggg                                                24

<210> SEQ ID NO 7
<211> LENGTH: 26
<212> TYPE: DNA
<213> ORGANISM: Mus sp.

<400> SEQUENCE: 7
agcggctgac tgaactcaga ttgtag                                              26

<210> SEQ ID NO 8
<211> LENGTH: 30
<212> TYPE: DNA
<213> ORGANISM: Mus sp.

<400> SEQUENCE: 8
cgtgttgatg aacatttgga caatgcgtat                                          30

<210> SEQ ID NO 9
<211> LENGTH: 29
<212> TYPE: DNA
<213> ORGANISM: Mus sp.

<400> SEQUENCE: 9
gccaactgga tagatgtaag atatgacct                                           29

<210> SEQ ID NO 10
<211> LENGTH: 25
<212> TYPE: DNA
<213> ORGANISM: Mus sp.

<400> SEQUENCE: 10
acattcgagg ctccagtgaa ttcgg                                               25
```

-continued

```
<210> SEQ ID NO 11
<211> LENGTH: 25
<212> TYPE: DNA
<213> ORGANISM: Mus sp.

<400> SEQUENCE: 11
ggcaggtcta ctttggagtc attgc                                              25
```

METHODS OF TREATING VIRAL INFECTIONS

The present invention relates to the use of strains of Parapoxvirus ovis as immunotherapeutic agents for immunodeficiencies of an infectious or non-infectious nature, and to the use of strains of Parapoxvirus ovis for treating tumour diseases and viral infections and diseases which accompany such infections, and the use of strains of Parapoxvirus ovis for producing medicaments for use in humans and animals.

The present invention furthermore relates to the use of strains of Parapoxvirus ovis, and of medicinal forms prepared therefrom, as immunotherapeutic agents or immunoprophylactic agents in stress metaphylaxis for preventing or averting infectious diseases following stress (e.g. operations); to their use in infection prophylaxis, for preventing or averting infectious diseases by means of administration prior to operations or interventions (e.g. before implantation of prostheses or before dental interventions), to their use in infection metaphylaxis or the therapy of acute or chronic viral infections, for example of the respiratory tract, of papilloma virus infections, of infection with herpesviruses, of HIV infection, and of viral infection of internal organs such as infection with hepatitis viruses, to their use in wound healing, in order to accelerate wound healing processes, and to their use for supporting the healing of wounds which only heal poorly or do not heal at all (e.g. ulcer of the leg), to their use for diseases such as multiple sclerosis, asthma, warts and other neoformations of the skin, to their use for diseases of the spectrum of allergic diseases, to their use for preventing the onset of systemic allergies, and to their use for topical allergies and to their use for improving wellbeing, for example in elderly patients, with the strains of Parapoxvirus ovis which are used within the context of the invention being the strains NZ2, NZ-7, NZ-10 and orf-11.

It is also possible to use descendants of these strains which have been obtained by passaging and/or adaptation to particular cells, for example WI-38, MRC-5 or Vero cells, or parts or fragments of viruses from these strains or of these descendants. Parts are to be understood as meaning genomic or subgenomic fragments which are expressed with the aid of suitable vectors, for example vaccinia, in suitable systems, for example fibroblast cell cultures. Fragments are understood as being the fractions, which are obtained by biochemical purification, for example by means of chromatography, of particles which have been physically disrupted, for example by means of ultrasonication.

The present invention furthermore relates to the use of the said strains of Parapoxvirus ovis for producing medicaments and pharmaceutical preparations. In addition to this, the invention relates to the use of the said strains of Parapoxvirus ovis, in combination with other remedies, for producing medicaments and pharmaceutical preparations for antiviral therapy or cancer therapy.

It is known that latent and chronic persistent viral infections can be activated or reactivated by an immunosuppression, or, conversely, that the immune system suppresses the acute disease which can be induced by a virus which is latent (e.g. a latent herpesvirus infection recurs in association with immunosuppression: labial blisters in association with stress or cortisone administration). It is furthermore known that chronically persistent and latent viral infections are difficult or even impossible to treat using conventional antiviral substances with a low molecular weight basis.

A reason for this can be the absence of viral enzymic activity in connection with such infections (for example the absence of any viral polymerase activity which firstly has to incorporate a nucleosidic inhibitor into the viral nucleic acid so that this inhibitor can, for example, give rise to chain termination in the viral DNA; for example the absence of any viral thymidine kinase activity, which firstly has, for example, to phosphorylate an antiviral compound so that this compound can become active), or else the lack of any recognition, by the immune system of the host, of infected or degenerate cells, for example cancer cells, or of viral antigens.

It is also known that, in association with chronically persistent viral infections, a superinfection with another virus can give rise to antiviral effects which are directed against the chronically persistent virus[1]. The authors[1] were able to demonstrate the dependence of this effect on interferons, such as IFN-γ and TNF-α, which are secreted by T cells, natural killer cells and macrophages.

The results obtained by these authors confirmed another, earlier study which demonstrated that Class I-restricted cytotoxic T cells were able to inhibit hepatocellular HBV gene expression in HBV-transgenic mice, that this process took place without any destruction of the liver cells, and that the process was elicited by TNF-α and IFN-γ[2].

A product for inducing "paraspecific immunity", i.e. what is termed a paraimmunity inducer, has been used therapeutically, metaphylactically and prophylactically in veterinary practice for a relatively long time. Paraimmunity inducers consist, for example, of chemically inactivated Parapoxvirus ovis, strain D 1701 (DE 3 504 940). BAYPAMUN® is a product which is prepared on the basis of this virus (Parapoxvirus ovis, strain D 1701).

In animals, the inactivated parapoxvirus induces nonspecific protection against infections caused by a very wide variety of pathogens. It is assumed that this protection is mediated by way of a variety of mechanisms forming part of the endogenous defence system.

These mechanisms include the induction of interferon, the activation of natural killer cells, the induction of "colony-stimulating activity" (CSA), and the stimulation of lymphocyte proliferation. Earlier investigations into the mechanism of action demonstrated the stimulatory effect of interleukin 2 and interferonα[3].

Against this background, the object therefore arises of further improving the therapeutic utility of the excellent effect of Parapoxvirus ovis so as to qualitatively increase the above-described generalized induction of a paraspecific immunoresponse by Parapoxvirus ovis, strain D 1701 and improve it such that better antiviral or anti-tumour effects can be achieved using lower doses. The therapeutic effect would then also be expected to have fewer side-effects.

The object of the invention was therefore to improve the immunological effect of Parapoxvirus. The object is achieved by using the abovementioned strains of Parapoxvirus ovis instead of the D1701 strain which is conventionally employed.

The present invention relates to the use of viruses which belong taxonomically to one of the Parapoxvirus ovis strains NZ2, NZ-7, NZ-10 or orf-11 for producing medicaments directed against viral infections and cancer in humans and animals.

The invention furthermore relates to the use of descendants of the strains according is to the invention, which descendants are obtained by passaging or adaptation to suitable cell systems, for example human cells, such as WI-38, MRC-5, monkey cells e.g. Vero cells, bovine cells such as BK-K13A47/Reg or MDBK, and ovine cells, such as MDOK, for producing medicaments against viral infections and cancer in humans and animals, and also relates to the use of parts or fragments of the said strains, and their passaging and adaptation variants, where parts are to be understood as being genomic or subgenomic fragments which are expressed with the aid of suitable vectors, such as vaccinia viruses, in suitable systems, such as fibroblast cell cultures and fragments are to be understood as being the fractions, which are obtained by biochemical purification, such as chromatography, of the expressed or physically disrupted viral particles, for producing medicaments which are directed against viral infections and cancer in humans and animals, and also relates to the use of one of the strains of Parapoxvirus ovis, and of derivatives which are derived as described above, for producing medicaments and pharmaceutical preparations as immunotherapeutic agents or immunoprophylactic agents for autoimmune diseases and for acute and chronic viral infections of the respiratory tract and the internal organs, and also relates to the use of one of the strains, and of derived derivatives, for producing medicaments and pharmaceutical preparations for stress metaphylaxis and for preventing or averting infectious diseases following stress and also in connection with infection prophylaxis within the context of operations and dental interventions, and also relates to the use of one of the strains, and of derived derivatives, for producing medicaments and pharmaceutical preparations for use in infection metaphylaxis or the therapy of acute and chronic viral infections, for example of the respiratory tract, of papilloma virus infections, of infection with viruses of the herpes group, of HIV infection, or of viral infection of internal organs, such as infection with hepatitis viruses, and also use in connection with diseases such as multiple sclerosis, asthma, warts and other neoformations of the skin, and also relates to the use of one of the strains, and of derived derivatives, for producing medicaments and pharmaceutical preparations for use on wounds, for accelerating wound healing processes, and use for supporting the healing of wounds which only heal poorly or which do not heal at all and ulcer of the leg, and also relates to the use of one of the strains, and of derived derivatives, for producing medicaments and pharmaceutical preparations for use for diseases of the spectrum of allergic diseases, psoriasis, neurodermatitis and other autoimmune diseases, such as lupus erythematodes, and also for improving wellbeing, for example in elderly patients, and also relates to the use of one of the strains, and of derived derivatives, for producing medicaments and pharmaceutical preparations for use against inflammatory, degenerative and proliferative diseases of the internal organs, for example Crohn's diseases, of the skin, of the blood, of the central nervous system and its appended structures, and including the eye, including cancer, and also relates to the use of one of the strains, and of derived derivatives, in combination with other remedies for producing medicaments and pharmaceutical preparations for antiviral therapy or cancer therapy in humans and animals.

The invention preferably relates to the use of one of the strains of Parapoxvirus ovis in combination with other remedies for producing medicaments and pharmaceutical preparations for oral administration, and/or in a gastric juice-resistant formulation for oral administration.

The following has been discovered by way of example:

1. Demonstration of Therapeutic Activity in Hepatitis B Virus—Transgenic Mice

Hepatitis B virus-transgenic mice (strain HBV 1.3×–tg) were used for the "proof-of-concept" experiment. 7 male animals, of from 8 to 10 weeks of age, were used per group. The various doses were administered intraperitoneally in a volume of 0.15 ml on day 1 (beginning of experiment) and on day 4.

For the administration, the following dilutions of each virus strain were prepared for the individual dose groups;

| | |
|---|---|
| 1st dose | $1.5 \times 10^6$ $TCID_{50}$ |
| 2nd dose | $5 \times 10^5$ $TCID_{50}$ |
| 3rd dose | $1.5 \times 10^5$ $TCID_{50}$ |
| 4th dose | $5 \times 10^4$ $TCID_{50}$ |

Sterile, pyrogen-free PBS was used as the placebo control.

The viruses were concentrated in the following manner: 500 ml of supernatant obtained from Parapoxvirus ovis strain NZ 2 (titre, approx. $2\times10^5$ $TCID_{50}$/ml) and Parapoxvirus ovis strain D 1701 (titre $1\times10^7$ $TCID_{50}$/ml) were adjusted to the same virus titre. A Beckman ultracentrifuge (SW28 rotor at 28000 RPM and 4° C. for 3 hrs) was used for this purpose. After the centrifugation, the pellets were adjusted to a titre of $1\times10^7$ $TCID_{50}$/ml using appropriate volumes of dilution medium.

Aliquots of the corresponding dosages were used for a verifying back titration, which confirmed the titres of these dosages. After the verification aliquots had been removed, the corresponding doses were inactivated at 56° C. for 1 hour.

| | |
|---|---|
| Dilution medium: | 10 ml EMEM 10x |
| | 2.7 ml of 2 g/l bicarbonate |
| | 1 ml of 1% glutamine |
| | 86.3 ml of double distilled water |

On day 5, the animals were sacrificed painlessly and the liver and blood were removed. Approximately 20 mg of liver from each animal were worked up using a QIAamp tissue kit (Qiagen, Hilden) and the concentration of the DNA was determined photometrically while its integrity was checked electrophoretically in a 1% agarose gel. The DNA was hybridized with an HBV-specific probe in a dot blot hybridization method. The DNA had previously been treated with RNAse A (Qiagen, Hilden) in order to exclude signals caused by RNA. 200 μl of DNA (10 μg) were loaded onto a nylon membrane (Boehringer Mannheim) and treated 4 times, for in each case 3 minutes, with Soak I (0.5N NaOH; 1M NaCl) and twice with Soak II (3M NaCl; 0.5M tris-HCl, pH 7.4); the DNA was then baked at 120° C. for half an hour and subsequently prehybridized, at 60° C. for 30 minutes, with a standard hybridization buffer (5×SSC, N-lauroylsarcosine, 0.1% w/v; SDS, 0.02%; blocking reagent, 1× and 100 μg of fish sperm DNA/ml) which did not contain any probe. Following this step, the DNA was hybridized with a random oligonucleotide-primed probe containing the entire HBV genome (20–40 ng/ml of hybridization buffer). After that, the filter was washed, at 64° C. for 10 minutes, in 4×SSC/0.1% SDS, 233 SSC/0.1% SDS and 1×SSC/0.1% SDS.

Immunological detection was effected using the CDP-Star® system (Boehringer Mannheim) in accordance with the manufacturer's instructions. A LumiImager® (Boehringer Mannheim) was used for the evaluation. HBV-specific DNA in the blood was quantified by means of quantitative PCR. The plasma was first of all isolated by centrifuging the EDTA blood. The DNA was purified using a HighPure 16 System Viral Nucleic Acid Kit (Boehringer Mannheim) and, by means of quantitative PCR, examined with the ABI PRISM™ 7700 Sequence Detection System (PE Applied Biosystems) for HBV-specific signals. The following primers and probe were employed:

```
ayw-570f (sense)      5'-CTGTACCAAACCTTCGGACGG-3'      (SEQ ID No:5)

ayw-670f (antisense)  5'-AGGAGAAACGGGCTGAGGC-3'        (SEQ ID No:4)

Probe:
ayw-613t              5'-CCATCATCCTGGGCTTTCGGAAAATT-3' (SEQ ID No:3)
```

The DNA was amplified in a reaction volume of 50 μl (the reaction contained 1.4 mM of each dNTP, 4.75 mM $MgCl_2$, 15 pmol of each primer and of the probe, 5 μl 10-times PCR buffer [all the PCR reagents were derived from the TaqMan core reagent kit; Perkin Elmer/Roche Molecular Systems Inc.] and 1.25 U of Taq DNA polymerase and 0.25 U of Amp Erase. After an initial denaturing step (10 min at 95° C.), the samples were subjected to 40 cycles of denaturation (95° C., 30 sec) and annealing/extension (56° C., 1 min). The products were analysed using the ABI PRISM™ 7700 Sequence Detection System standard software.

A histochemical analysis was carried out using antibodies directed against the hepatitis B virus core antigen (Dako). For this, parts of one liver lobe were fixed overnight in 4% formaldehyde, embedded in paraffin and sectioned (5 μm). After removal of the paraffin and rehydration, the endogenous peroxidase activity was quenched for a period of 20 minutes using 3% $H_2O_2$. Nonspecific binding was blocked with normal sheep serum. The sections were then incubated at room temperature for 30 minutes with the antibody, which was diluted 1:500. All the subsequent steps were carried out using the Vectastain ABC kit (Vector Laboratories) as described by the manufacturer.

The immune reaction was visualized using 3,3'-diaminobenzidine tetrachloride and hydrogen peroxide. The sections were counterstained with haematoxylin/eosin.

The results were analysed statistically by means of analysis of variance and post hoc comparison.

In conclusion, it was found, surprisingly, that an amplification of the antiviral effect, as compared with that obtained with the known Parapox ovis strain D 1701, is achieved when the strain NZ2 is used. This makes it possible, for the first time, to use Parapoxvirus ovis to induce the complex capacity of the immune system with an intensity which differs significantly from the intensity of the effect achieved with the previously known paraimmunity inducers.

The following results were surprisingly obtained:

Liver: A significantly greater reduction of HBV-specific DNA was observed in animals treated with NZ2 as compared with animals treated with D 1701. The antiviral activity of NZ2 is more potent than that of D 1701: in the highest dose group, administration of NZ2 reduces the HBV-specific DNA more than 45 times more effectively than does administration of the same quantity of D 1701, while, in the lowest dose group, it reduces it 57 times more effectively. In plasma, administration of NZ2 reduces the HBV-specific DNA, in the lowest dose group, more than 10 times more effectively than does administration of the same quantity of D 1701. This demonstrated that the therapeutic efficacy of Parapoxvirus ovis strain NZ2 is significantly superior to that of strain D 1701.

In the figures, the reduction of HBV-specific signals is shown in comparison with the placebo group (this was equated with 100%).

FIG. 1 shows results of treating HBV-transgenic mice with strain D 1701 or NZ2. While HBV-specific DNA is significantly reduced in the liver, as compared with the placebo group, with both strains and in all dose groups, the reduction is greater when strain NZ2 is used. At both the lowest NZ2 doses, the reduction in HBV-specific DNA is significantly greater than in the case of the equivalent D 1701 dose groups.

FIG. 2 shows the result, obtained in the plasma, of treating HBV-transgenic mice with strain D701 or NZ2. While HBV-specific DNA is significantly reduced in the plasma, as compared with the placebo group, with both strains and in all dose groups, the reduction is greater when strain NZ2 is used. In contrast to the lowest dose of NZ2, the lowest dose of strain D 1701 no longer has a significant antiviral effect.

2. Induction of Cytokines 7 to 8-week-old female Balb/c mice were kept under sterile conditions and used for the experiment. The animals were randomized and divided up into groups which each contained 6 animals. The following treatment scheme was applied:

| | |
|---|---|
| Group 1: | Placebo |
| Group 2: | *Parapoxvirus ovis* strain D 1701; 5 × $10^4$ $TCID_{50}$/dose |
| Group 3: | *Parapoxvirus ovis* strain NZ2; 5 ×$10^4$ $TCID_{50}$/dose |
| Group 4: | Placebo |
| Group 5: | *Parapoxvirus ovis* strain D 1701; 5 × $10^4$ $TCID_{50}$/dose |
| Group 6: | *Parapoxvirus ovis* strain NZ2; 5 × $10^4$ $TCID_{50}$dose |

The volume administered was 10 ml/kg, with the administration taking place intraperitoneally.

The animals in groups 1 to 3 were sacrificed 6 hours after the administration, while the animals in groups 4 to 6 were sacrificed 12 hours after the administration; peritoneal cells were obtained by means of a lavage using ice-cold PBS, and the portal and mesenteric lymph nodes were isolated.

The peritoneal cells were concentrated by means of a centrifugation step (5 min at 3000 rpm and room temperature in an Eppendorf bench centrifuge) and subsequently taken up in 0.2 ml of lysis buffer (lysis solution: 25 mM sodium citrate, 4 M guanidinium isothiocyanate, 0.5% N-lauroylsarcosine), shock-frozen and stored at −75° C. until it was time to prepare the RNA.

The total RNA was prepared by means of acidic phenol/chloroform extraction. For this, the samples which had been frozen in lysis buffer were thawed at room temperature and treated, for the extraction, with the following solutions: 1/10th of the lysis buffer volume of 2 M sodium acetate (pH 4.0), 1 lysis buffer volume of water-saturated phenol and 1/5th of the lysis buffer volume of chloroform/isoamyl alcohol (24:1). These ingredients were mixed on a vortexer for 10 seconds and then brought to constant temperature by being kept for 10 minutes on ice. The phases were separated by centrifuging at 15365 g and 4° C. for 30 minutes. After that, the aqueous phase was transferred into a new vessel and 8 ml of RNA-MATRIX, from the Rnaid™ plus kit (DIANOVA), were added, in order to isolate the RNA present in this phase, and the whole was incubated at room temperature for 15 minutes. The resulting RNA/RNA-MATRIX complex was pelleted by centrifugin at 7000 g and the supernatant was discarded. The pellet was subsequently washed 2× with in each case 250 ml of RNA-WASH (DIANOVA) and, after the last wash, dried by vacuum centrifugation. The RNA was eluted by adding 20–30 ml of RNAse-free distilled water and heating the whole at a temperature of 55° C. for 15 minutes. After centrifuging at 7000 g and room temperature for 1 minute, the matrix was separated off by transferring the RNA solution to a new vessel.

The quality of the RNA was checked by means of gel electrophoresis. The RNA was stored at −70° C.

The cDNA was synthesized by reverse-transcribing the mRNA using oligo(dT) primers as starter molecules for the polymerization. The following components were present in the synthesis mixture: 200 ng–2 µg of total RNA, 2 µl of M-MLV reverse transcriptase (200 U/µl) (GIBCO/BRL), 8 µl of the pertinent 5×RT buffer (GIBCO/BRL), 1 µl of DTT (0.1M) (GIBCO/BRL), 4 µl of dNTP (2.5 mM) (SIGMA), 2 µl of oligo(dT)$_{12-18}$ primer (100 µg/ml) (PROMEGA), 1 µl of human placental RNAse inhibitor (10000 U/ml) (GIBCO/BRL) and water to 40 µl total volume. The mixture was kept at room temperature for 10 minutes and then incubated at 37° C. for 45 minutes; it was then heated at 95° C. for 3 minutes and immediately cooled on ice. The CDNA was which synthesized in this way was stored at −20° C.

Figure 4:
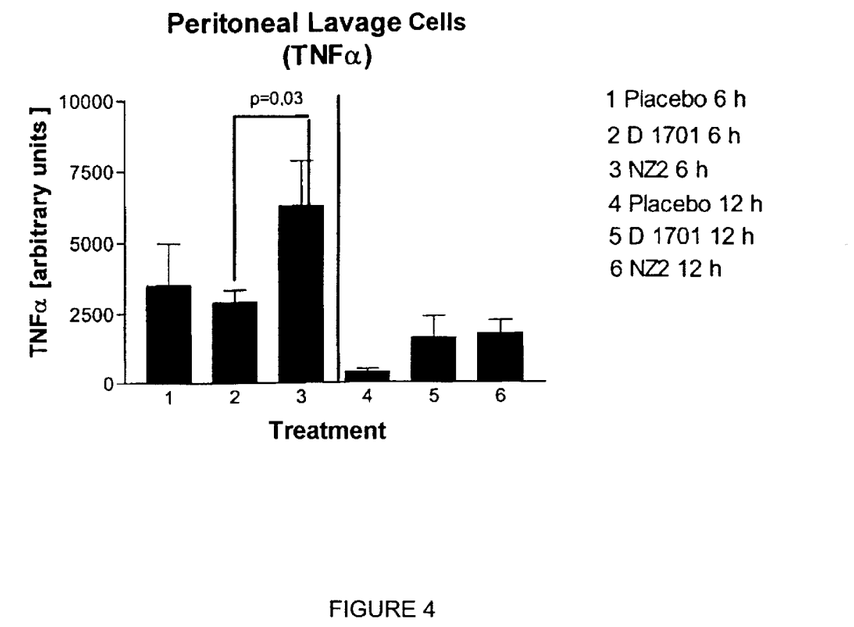

The quantities of the cDNAs were standardized using a "housekeeping" gene (β-actin). The quantitative PCR was carried out using the ABI PRISM™ 7700 Sequence Detection System (PE Applied Biosystems). The following primers were employed:

administration, while it is induced at 6 and 12 hours after administration following treatment with strain NZ2 (with it already being possible to observe a decrease, as compared with the 6-hour value, after 12 hours; FIG. 4). In the case of strain NZ2, this induction at 6 hours after administration is significantly higher than that observed in the case of strain D 1701. The figure depicts the values which were measured in cells which were obtained by peritoneal lavage.

Figure 5:
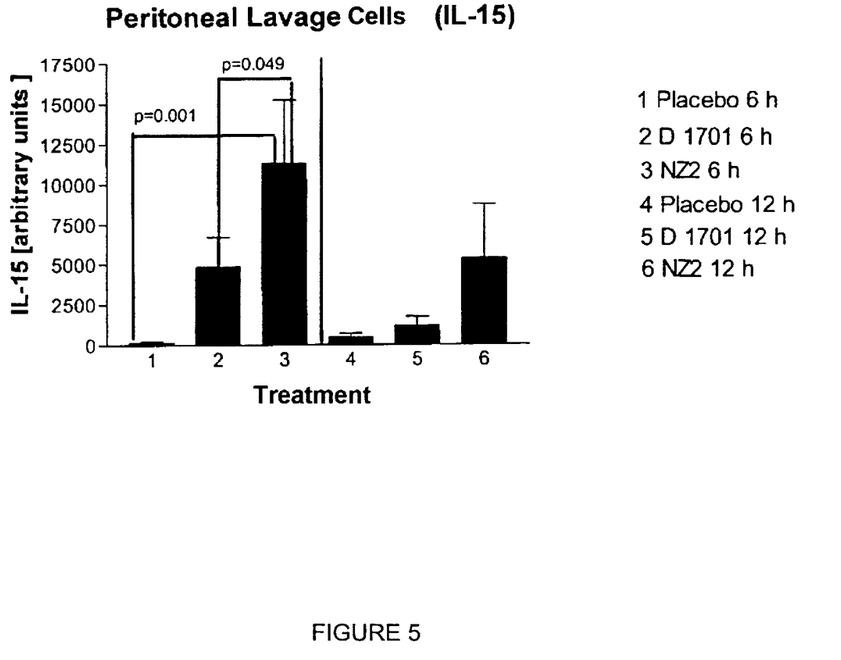

3. Following treatment with strain D 1701 or strain NZ2, the expression of IL-15 is induced at both 6 and 12 hours after the administration (FIG. 5). In the case of strain NZ2, this induction is significantly higher, at 6 hours after administration, than in the case of strain D 1701 or the placebo. The magnitude of IL-15 expression which is observed following administration of D 1701 is not significantly higher than that observed in the placebo control. The figure depicts the values which were measured in cells obtained by peritoneal lavage.

3. Demonstration of Therapeutic Efficacy in Tumour-Bearing Nude Mice

MDA-MB231 cells (ATCC#HTB26) were cultured, at 37° C. and in the presence of 5% $CO_2$, in complete medium (88 5 DMEM, 10% FBS, 1% penicillin/streptomycin, 1% L-glutamine (in each case Gibco Life Technologies)) in an incubator. On the day of the transplantation, the cells were approx. 70% confluent. The cells were trypsinized, washed with HBSS, counted and adjusted to $2.5 \times 10^7$ cells/ml using

```
β-Actin    sense:      5'-TGG AAT CCT GTG GCA TCC ATG AAA C-3'      (SEQ ID No:2)
           antisense:  5'-TAA AAC GCA GCT CAG TAA CAG TCC G-3'      (SEQ ID No:1)

IFN-γ      sense:      5'-AGCGGC TGA CTG AAC TCA GAT TGT AG-3'     (SEQ ID No:7)
           antisense:  5'-GTC ACA GTT TTC AGC TGT ATA GGG-3'        (SEQ ID No:6)

TNF-α      sense:      5'-GGC AGG TCT ACT TTG GAG TCA TTG C-3'     (SEQ ID No:11)
           antisense:  5'-ACA TTC GAG GCT CCA GTG AAT TCG G-3'     (SEQ ID No:10)

IL-15      sense:      5'-GCC AAC TGG ATA GAT GTA AGA TAT GAG CT-3' (SEQ ID No:9)
           antisense:  5'-CGT GTT GAT GAA CAT TTG GAC AAT GCG TAT-3' (SEQ ID No:8)
```

The DNA was amplified in a reaction volume of 25 µl (the reaction contained 1.4 mM of each dNTP, 4 mM $MgCl_2$, 0.3 µmol of each primer and of the probe, 2.5 µl of 10-times PCR buffer containing SYBR Green [all the PCR reagents were derived from the SYBR Green PCR core reagent kit; Perkin Elmer/Roche Molecular Systems Inc.] and 1.25 U of Taq DNA polymerase and 0.25 U of Amp Erase. After an initial denaturation step (95° C. for 10 min), the samples were subjected to 40 cycles of denaturation (95° C. 30 s) and annealing/extension (60° C., 1.30 min). The products were analysed using the ABI PRISM™ 7700 Sequence Detection System Standard Software. The results were analysed statistically by analysis of variance and post hoc comparison.

Figure 1:
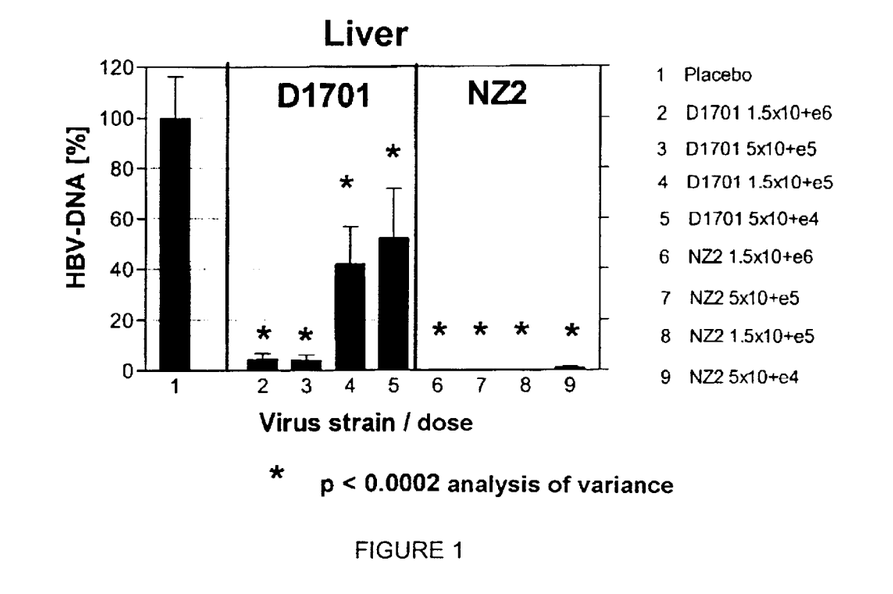
Figure 2:
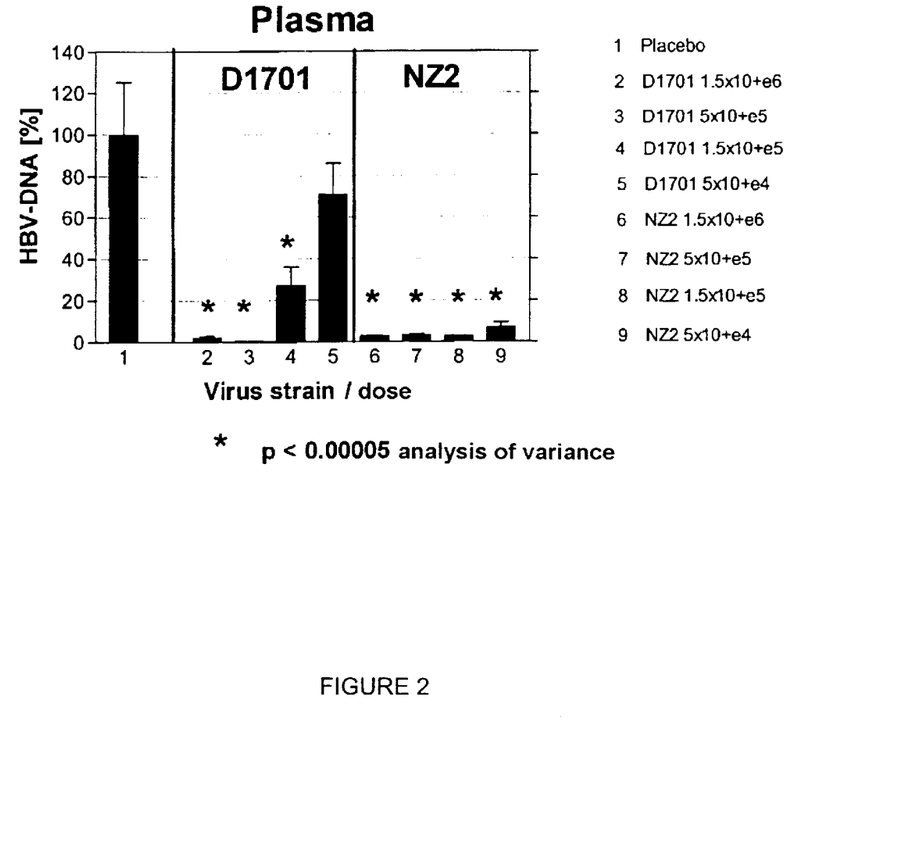
Figure 3:
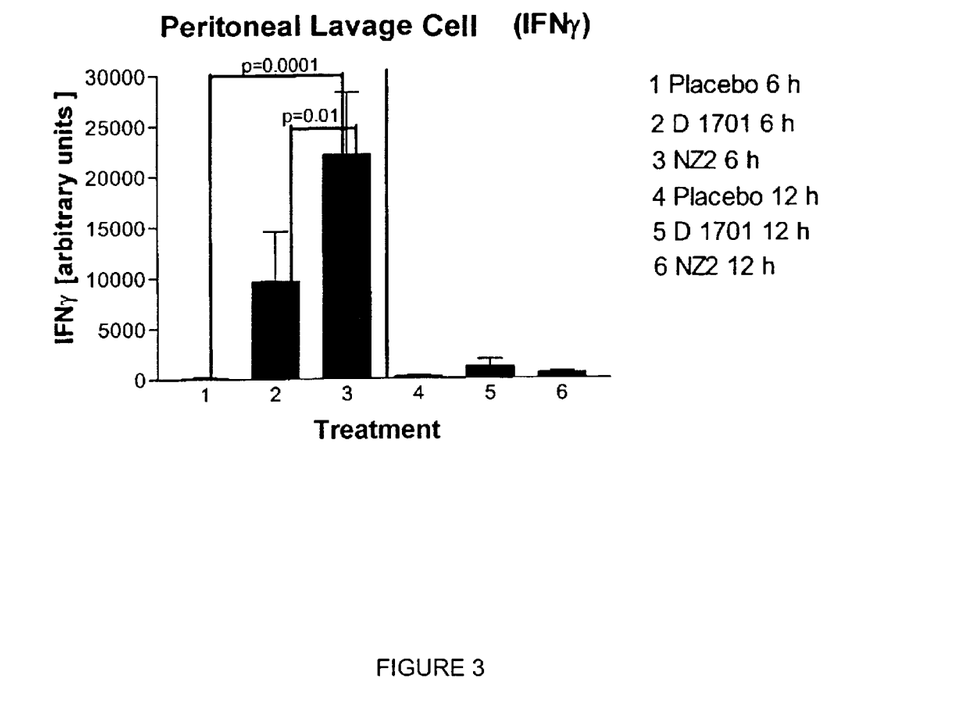

The following results were surprisingly obtained:

1. After treating with strain D 1701 or strain NZ2, the expression of γ interferon is induced at both 6 and 12 hours after the administration (FIG. 3). In the case of strain NZ2, this induction is significantly higher both in relation to the placebo and in relation to strain D 1701. The magnitude of γ interferon expression which is observed following the administration of D 1701 is not significantly different from that of the placebo control. The figure depicts the values which were measured in cells obtained by peritoneal lavage.

2. Following treatment with strain D 1701, the expression of TNF α is induced at 12 hours after the precooled PBS. Female NCr nude mice (taconic) were used. The mice were between 8 and 10 weeks of age and weighed approx. 22 g. All the manipulations on the animals were carried out under sterile conditions. $5 \times 10^6$ cells were injected subcutaneously into the flank region in a total volume of 0.2 ml. After that, the mice were kept for a further seven days until the tumours had reached an average mass of approx. 80 mg. The tumours were measured and the mice were divided randomly into three groups of in each case 10 animals. The following were administered to the individual groups:

| | |
|---|---|
| Group 1: | Placebo (PBS) |
| Group 2: | *Parapoxvirus ovis*, strain D1701 |
| Group 3: | *Parapoxvirus ovis*, strain NZ2 |

D1701 was administered in a dose of $2.5 \times 10^5$ $TCID_{50}$, while NZ2 was administered in a dose of $1 \times 10^5$ $TCID_{50}$; these doses were in each case administered four times in all at intervals of in each case three days. The tumours were measured twice weekly. Significances were determined using Student's test.

Figure 6:
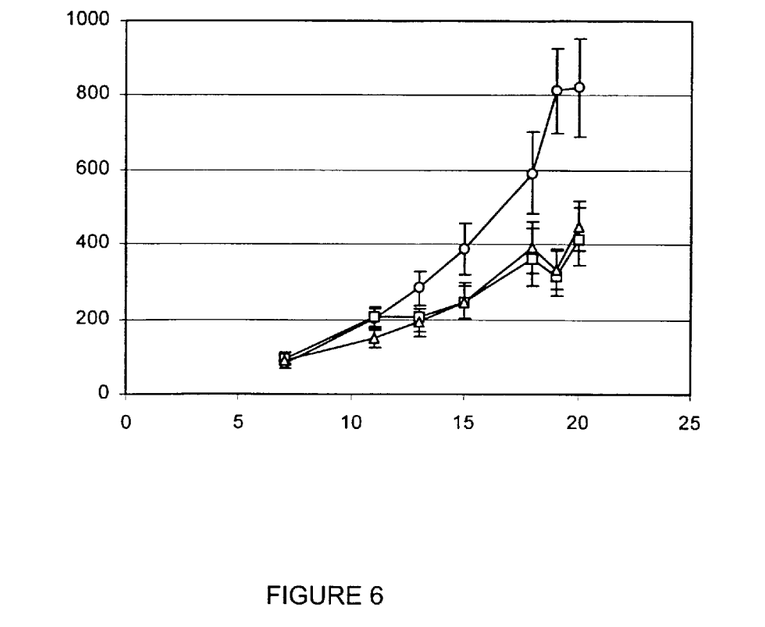
Figure 7:
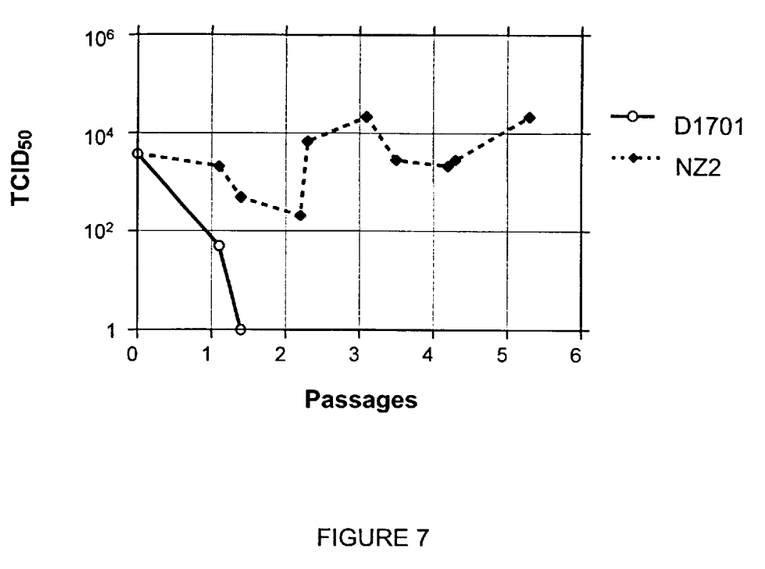
Figure 8:
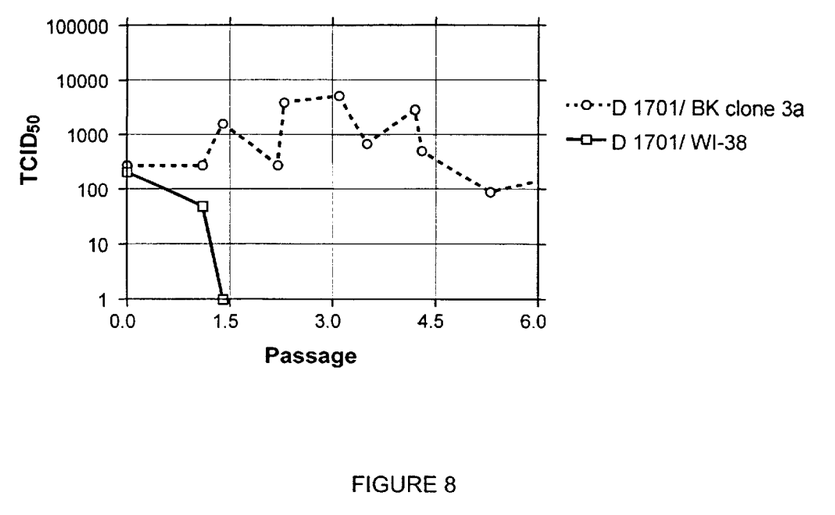
Figure 9:
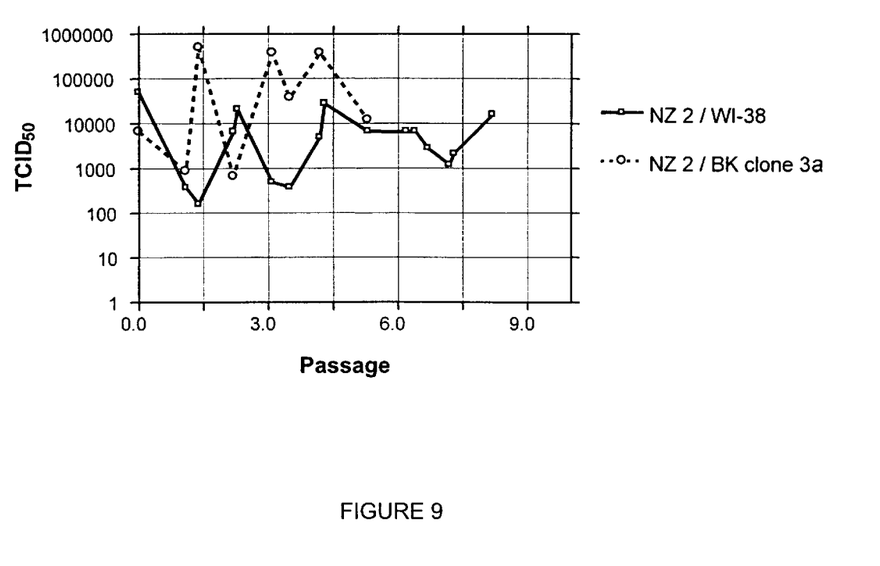
Figure 10:
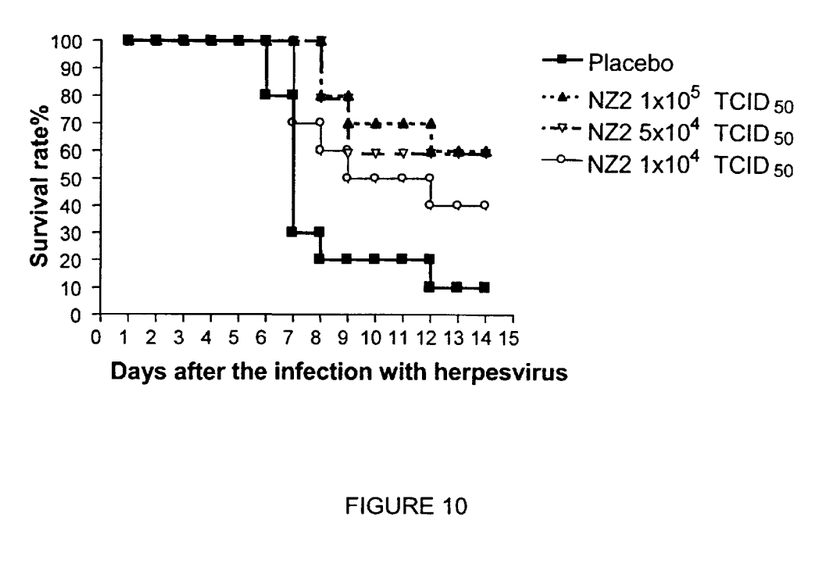

FIG. 6 shows the mean size of the tumours (in milligrams) in animals belonging to Groups 1 to 3 over the experimental period (in days). (Symbols: Group 1, circles, Group 2, triangles; Group 3, squares)

Surprisingly, an activity directed against tumours, which activity was significant (p<0.05) as compared with the control group, was found in the experimental system. The NZ2 strain was found to be markedly more potent in this regard than the strain D1701. Only about half the quantity of NZ2, as compared with D1701, was required in order to achieve the same effect.

This finding provides clear substantiation of the therapeutic efficacy of virus preparations according to the invention in tumour-bearing nude mice.

Nude mice are immunodeficient and do not possess any functional T cells. In the experimental system, the activity which is directed against tumours is presumably due to the natural killer (NK) cells, to other cells and to the direct effect of cytokines/chemokines. The superior efficacy of NZ2 would be expected to be even more clearly evident in the case of an immune system which was complete and intact.

4. Other Biological Differences Between NZ2 and D1701

It was found that, in contrast to strain D1701, Parapox virus NZ2 can be continuously passaged on human cell lines. This demonstrates fundamental differences between NZ2 and D1701 in replication behaviour and/or in the viral receptors.

Adaptation to human cell lines is an important prerequisite for the production of viral strains on human cell lines.

4.a) Ability to be passaged continuously on human MRC-5 cells.

FIG. 7 depicts an attempt to adapt strains NZ2 and D1701 to the human diploid cell line MRC-5. MRC-5 is suitable for producing biological active compounds and vaccines. The same starting titre was employed for both strains and the corresponding cell culture supernatants were continued over 5 passages in MRC-5 cells. The figure depicts the titre, in $TCID_{50}$, of samples from supernatants from the MRC-5 cells which were in each case infected, plotted against the passage number. Only strain NZ2, and not D1701, was back-titratable on bovine kidney cell cultures (BK clone 3a). This points to the presence of fundamental biological differences between the two strains in their infection and replication behaviour. At the same time, this result shows that NZ2 can be replicated in a broader spectrum of cells than D1701, thereby giving rise to the possibility of a production process which is based on human cells.

4.b) Ability of NZ2 and D1701 to be passaged on WI-38 cells and BK clone 3a cells.

Fundamental biological differences between the strains NZ2 and D1701 are also clearly demonstrated by the experiments depicted in FIG. 8 and FIG. 9. FIG. 8 shows the virus titre obtained in attempts to passage D1701 on bovine BK clone 3a cells and on human WI-38 cells, plotted against the number of passages. It can be seen that D1701 can be continuously passaged on BK clone 3a cells but not on human WI-38 cells.

The situation is different with the NZ2 strain. This strain can be passaged continuously over several days both on BK clone 3a cells and on WI-38 cells (FIG. 9).

These results also point to distinct differences in the infection and replication behaviour of NZ2 and D1701.

4.c) Dose-dependent effect of NZ2 in the herpesvirus challenge test following passaging on WI-38.

Herpesvirus challenge tests were carried out on mice in order to investigate the immunostimulatory properties of NZ2 strains which had been passaged on WI-38 cells. Three groups of in each case 10 experimental animals were treated with $1\times10^4$ $TCID_{50}$, $5\times10^4$ $TCID_{50}$ and $1\times10^5$ $TCID_{50}$, respectively, while a control group was given a placebo. FIG. 10 depicts the survival rate of the four experimental groups over time following the infection with herpesvirus. It was found, surprisingly, that NZ2 did not lose its immunostimulatory properties as a result of the passage on WI-38 cells.

All the experimental results in this example point to fundamental biological differences in the infection and replication behaviour of NZ2 and D1701. It was found, surprisingly, that, in contrast to the situation with D1701, the preparation of NZ2 for use as an immunomodulator is not bound to the use of bovine kidney cells as the production cell line.

Based on the known circumstances of the influence of a Th1 immune response on latent and chronically persistent virus infections[4,5] and also proliferative diseases, e.g. cancer[8,9], and the fact that the immunomodulatory properties of Parapoxvirus ovis strain NZ2 are superior to those of Parapoxvirus ovis strain D1701, the use of immunomodulators based on Parapoxvirus ovis strain NZ2, or one of the abovementioned strains, as a monotherapy or in combination with biologically active, e.g. antiviral, low-molecular weight compounds, in humans and animals is possible and of therapeutic utility for the antiviral therapy of infections with hepatitis B virus or hepatitis C virus or any of the other pathogens from the group of hepatitis-causing viruses, and also other viral infections of the internal organs, and also infections, accompanied by other diseases as well, with the various types of herpes simplex virus (HSV), the various types of human papillomavirus (HPV), human immunodeficiency virus (HIV), varicella zoster virus, human cytomegalovirus (HCMV) and the corresponding virus diseases in animals.

Furthermore, on the basis of the mechanism of action which has been demonstrated, the abovementioned strains of Parapoxvirus ovis can be used, with some prospect of success, for carrying out the following prophylactic or therapeutic treatments, in particular:

Prevention of recurrences in connection with herpesvirus infections, metaphylaxis, i.e. prevention of the establishment of viral infections (e.g. HIV), when treatment with the remedy is effected immediately after exposure[7)]. On the basis of the mechanism of action, it is likewise possible to treat cancer[8,9)].

Depending on the nature of the clinical problem, the parapoxvirus-based therapeutic agent is administered either systemically, that is, for example, intrasmuscularly, subcutaneously, intraperitoneally, intravenously or orally, or else locally. In this connection, the parapoxvirus is either present in the purified and lyophilized state and/or is suspended in a suitable solvent immediately prior to administration, or else is present in another suitable formulation or is present in a gastric juice-resistant administration form or another oral administration form.

Suitable preparations can also be produced from NZ2 descendants which are obtained by passaging and/or adaptation to particular cells, for example WI-38, MRC-5 or Vero cells, and the other abovementioned strains or parts or fragments of NZ2, and the other abovementioned strains or their descendants. Parts are to be understood as being genomic or subgenomic fragments which are expressed with the aid of suitable vectors, for example vaccinia, in suitable systems, for example fibroblast cell cultures. Fragments are understood as being the fractions, which are obtained by biochemical purification, for example chromatography, of particles which are disrupted physically, for example by means of ultrasonication.

In this connection, several administrations, or long-term treatment in accordance with chronological schemes which meet the requirements of the clinical problem, may be necessary.

Thus, use in accordance with the following scheme has proved to be particularly promising in the case of cancer therapy, for example (but without any restriction):

Intramuscular administration of in each case from $10^6$ to $10^7$ TCID$_{50}$ (tissue culture infective dosage) on every 3rd day for 4 weeks, followed by a pause of 2 weeks; renewed intramuscular administration of in each case from $10^6$ to $10^7$ TCID$_{50}$ on every 3rd day for 4 weeks followed by a pause of 2 weeks; renewed intramuscular administration of in each case from $10^6$ to $10^7$ TCID$_{50}$ on every 3rd day for 4 weeks, followed by a pause of 2 weeks; depending on the severity and the success of the therapy, these cycles can be supplemented with further cycles; alternatively, a scheme may be indicated under which the formulation is administered every 4th to 5th day over at least 3 months.

For example, in the case of chronic viral infection, from $10^6$ to $10^7$ TCID$_{50}$ of the formulation are administered subcutaneously in the abdominal region, or intramuscularly in the region of the deltoid or quadriceps, every 3rd day for a total of 5 times in all. It is possible to deviate from this scheme depending on the needs arising from the disease. For the prophylaxis of colds, the formulation has to be used for gargling and this has to be repeated daily as long as there is a risk of contagion.

In order to prevent infections following surgical interventions in the oral region (e.g. dental operations), gargling has to be performed with the formulation for 1–2 min. on the evening prior to the intervention.

The Parapox Virus NZ-2 used here as an example has been deposited with the European Collection of Cell Cultures, Centre for Applied Microbiology and Research, Porton Down, Salisbury, Wiltshire, SP4 OJG, United Kingdom on July 10th 2001. The number of the deposit is 01071006.

References

1. Guidotti, L. G., Borrow, P., Hobbs, M. V., Matzke, B., Gresser, I., Oldstone, M. B. A., and Chisari, F. V. (1996): Viral cross talk: Intracellular inactivation of the hepatitis B virus during an unrelated viral infection of the liver. Proc. Natl. Acad. Sci. USA. 93:4589–4594.
2. Guidotti, L. G., Ando, K., Hobbs, M. V., Ishikawa, T., Runkel, L., Schreiber, R. D., and Chisari, F. V. (1994): Cytotoxic T lymphocytes inhibit hepatitis B virus gene expression by a noncytolytic mechanism in transgenic mice. Proc. Natl. Acad. Sci. USA. 91:3764–3768.
3. Steinmassl, G., G. Wolf (1990): Bildung von Interleukin 2 und Interferon-durch mononukleäre Leukozyten des Schweines nach in vitro-Stimulation mit verschiedenen Viruspräparaten (Formation of interleukin 2 and interferon by pig mononuclear leukocytes following in-vitro stimulation with various virus preparations). J. Vet. Med. B 37,5,321–331.
4. P. Lucin, S. Jonjic, M. Messerle, B. Polic, H. Hengel, U. H. Koszinowski (1994): Late-Phase inhibition of murine cytomegalovirus replication by synergistic action of interferon gamma and tumor necrosis factor alpha. J. Gen. Virol 75:101–110; P.M.
5. Smith, R. M. Wolcott, R. Chervenak, S. R. Jennings (1994): Control of acute cutaneous herpes-simplex virus-Infection-T-cell mediated viral clearance is dependent upon interferon gamma. Virology 202 (1):76–88].
6. Y. Kawanashi, N. Hayashi, K. Katayama, K. ueda, T. Takehara, E. Miyoshi, E. Mita, A. Kasahara, H. Fusamoto, T. Kamada (1995): Tumor necrosis factor alpha and interferon gamma inhibit synergistically viral replication in hepatitis B virus replicating cells. J. Medical Virology 47 (3):272–277.
7. Dhawan, S., L. M. Wahl, A. Heredia, Y. H. Zhang, J. S. Epstein, M. S. Meltzer, I. K. Hewlett (1995): Interferon gamma inhibits HIV-induced invasiveness of Monocytes. J. Leukocyte Biology, 58 (6):713–716.
8. J. F. Bromberg, C. M. Horvath, Z. L. Wen, R. D. Schreiber, J. E. Darnell (1996): Transcriptionally active stat1 is required for the antiproliferative effects of both interferon alpha and interferon gamma. PNAS 93(15):7673–7678.
9. M. Klouche, H. Kirchner, F. Holzel (1994): Antiproliferative effects of interferon gamma in combination with alpha-difluoromethylornithine on human carcinoma cell cultures. J. Cancer Research and Clinical Oncology 120 (12):706].

What is claimed is:

1. A method of treating viral infections in humans and animals, comprising administering to a human or animal an effective amount of a virus which belongs taxonomically to the Parapoxvirus ovis strains NZ2.

2. The method of claim 1, wherein said Parapoxvirus ovis strain is a descendant obtained by passaging or adaptation to a suitable cell system.

3. The method of claim 1, wherein said Parapoxvirus ovis strain comprises parts or fragments of the virus.

4. A method of treating chronic viral infections, comprising administering to a human or animal an effective amount of the strains of Parapoxvirus ovis NZ2.

5. The method of claim 4, wherein said chronic viral infection is selected from the group consisting of respiratory tract infections, papilloma virus infections, infection with herpesviruses, HIV infection, or viral infection of internal organs.

6. The method of claim 2, wherein said suitable cell system is selected from human cells WI-38 and MRC-5, Vero cells, bovine cells BK-K12A47/Reg and MDBK, and ovine cells MDOK.

7. The method of claim 3, wherein said parts of the virus are genomic or subgenomic fragments expressed with the aid of a vector in a suitable system.

8. The method of claim 7, wherein said vector is vaccinia virus and said suitable system is a fibroblast cell culture.

9. The method of claim 3, wherein said fragments are fractions obtained by biochemical purification of expressed or physically disrupted viral particles.

10. The method of claim 9, wherein said biochemical purification is chromatography.

11. The method of claim 5, wherein said infection of internal organs is infection with hepatitis virus.

* * * * *